United States Patent [19]

Neh et al.

[11] Patent Number: 4,888,340
[45] Date of Patent: Dec. 19, 1989

[54] INSECTICIDES PYRAZOLINES, COMPOSITIONS AND USE

[75] Inventors: Harribert Neh; Ulrich Bühmann; Peter Wegner; Hartmut Joppien; David Giles, all of Berlin, Fed. Rep. of Germany; Graham P. Rowson, Hundon, Great Britain

[73] Assignee: Schering Aktiengesellschaft, Fed. Rep. of Germany

[21] Appl. No.: 248,255

[22] Filed: Sep. 20, 1988

Related U.S. Application Data

[63] Continuation of Ser. No. 945,361, Dec. 22, 1986, abandoned.

[30] Foreign Application Priority Data

Dec. 21, 1985 [DE] Fed. Rep. of Germany ....... 3545786
Aug. 22, 1986 [DE] Fed. Rep. of Germany ....... 3628647

[51] Int. Cl.⁴ .................... A01N 43/56; C07D 231/06
[52] U.S. Cl. ..................................... 514/403; 548/379
[58] Field of Search ....................... 548/379; 514/403

[56] References Cited

U.S. PATENT DOCUMENTS 4,407,813 10/1983 Ozawa et al. .................. 548/379
4,540,706 9/1985 Ozawa et al. .................. 548/379
4,572,914 2/1986 van Hes et al. ................. 514/403

*Primary Examiner*—Robert W. Ramsuer
*Attorney, Agent, or Firm*—Ostrolenk, Faber, Gerb & Soffen

[57] ABSTRACT

Compounds of formula I

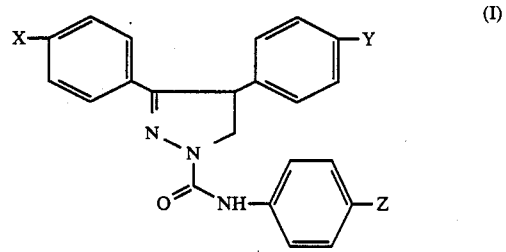

in which X, Y and Z have various meanings, are described, as well as processes for their preparation and their use as insecticides and acaricides.

9 Claims, No Drawings

INSECTICIDES PYRAZOLINES, COMPOSITIONS AND USE

This is a continuation of application Ser. No. 945,361 filed on Dec. 22, 1986, now abandoned.

The present invention relates to new pyrazoline derivatives, their preparation and their use as pesticides.

Pyrazolines with insecticidal activity are already known (see for example EP 21506, EP 58424, EP 113213 and GB No. 1514285.

The object of the present invention is to provide pyrazoline derivatives that have a greater activity and better selectivity.

The pyrazoline compounds of the invention are of general formula I

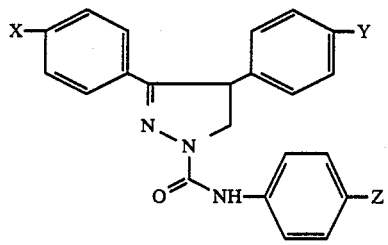

(I)

in which (i) Z is hydrogen, halogen, $C_{1-4}$-alkyl, trifluoromethyl, $C_{1-4}$-alkoxy, $C_{1-4}$-alkoxycarbonyl, halo-$C_{1-4}$-alkoxy, $C_{1-4}$-alkylthio, halo-$C_{1-4}$-alkylthio, halo-$C_{1-4}$-alkylsulphinyl, halo-$C_{1-4}$-alkylsulphonyl, 2,2-dihalocyclopropyloxy or 2,2-dihalocyclopropylmethoxy, and either (a) X is 2,2-dihalocyclopropylmethoxy; phenoxy; phenylthio, pyridyloxy; halo-$C_{2-4}$-alkenyloxy, halo-$C_{1-4}$-alkylthio; halo-$C_{1-4}$-alkenylthio; halo-$C_{1-4}$-alkylsulphinyl or halo-$C_{1-4}$-alkylsulphonyl; said phenoxy or phenylthio being optionally substituted by one or more of the same or different groups selected from halogen, $C_{1-4}$-alkyl, $C_{1-4}$-alkoxy, halo-$C_{1-4}$-alkyl and halo-$C_{1-4}$-alkoxy, and said pyridyloxy being optionally substituted by one or more of the same or different groups selected from halogen and trifluoromethyl, and Y, which may be the same or different from X, has the same meanings as X or can be hydrogen, halogen, $C_{1-4}$-alkyl, trifluoromethyl, $C_{1-4}$-alkoxy or halo-$C_{1-4}$-alkoxy, or (b) X has the has the same meanings given for Y under (a) and Y has the same meanings given for the X under (a), or (ii) Z is 2,2-dihalocyclopropyloxy or 2,2-dihalocyclopropylmethoxy, and X and Y are the same or different and are hydrogen, halogen, $C_{1-4}$-alkyl, trifluoromethyl, $C_{1-4}$-alkoxy or halo-$C_{1-4}$-alkoxy, or (iii) Z is hydrogen, halogen, $C_{1-4}$-alkyl, trifluoromethyl, $C_{1-4}$-alkoxy, $C_{1-4}$-alkoxycarbonyl, halo-$C_{1-4}$-alkoxy, $C_{1-4}$-alkylthio, halo-$C_{1-4}$-alkylthio, halo-$C_{1-4}$-alkylsulphinyl or halo-$C_{1-4}$-alkylsulphonyl, X is halo-$C_{2-4}$-alkoxy and Y is hydrogen, halogen, $C_{1-4}$-alkyl, trifluoromethyl or $C_{1-4}$-alkoxy.

When alkyl, alkoxy, alkylthio, alkenyloxy, alkenylthio, alkylsulphinyl or alkylsulphinyl are substituted by halogen, this may be by one or more halogen atoms. By the term halogen is meant especially fluorine, chlorine and bromine.

Examples of halo-$C_{1-4}$-alkoxy groups are difluoromethoxy, 2,2,2-trifluoroethoxy and 1,1,2,2,-tetrafluoroethoxy.

A particularly preferred group of compounds are those where Z is halo-$C_{1-4}$-alkoxy and especially difluoromethoxy. It is generally preferred that Y is halogen, especially fluorine. It is also preferred that X is 2,2,2-trifluoroethoxy or 2,2-difluorocyclopropylmethoxy.

The invention includes all isomeric forms and mixtures of these. The compound of the invention of formula I can be prepared by reacting a pyrazoline of general formula II

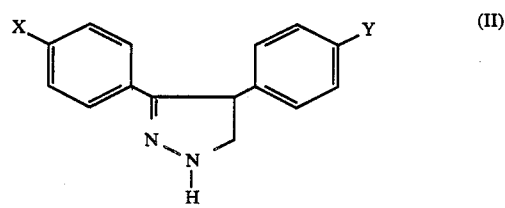

(II)

either (A) with an isocyanate of formula III

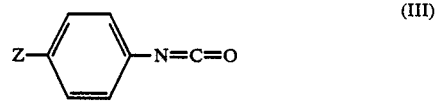

(III)

optionally using a solvent, or (B) with the reaction product from trichloromethyl chloroformate and an aniline of formula IV

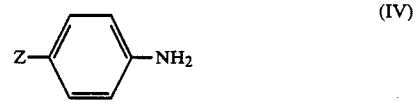

(IV)

optionally using a solvent, in which X, Y and Z have the meanings given in formula I.

Suitable solvents are liquids which are inert to the reactants such as for example aliphatic, alicyclic and aromatic hydrocarbons, which can be optionally chlorinated, e.g. hexane, cyclohexane, petroleum ether, benzene, toluene, xylene, dichloroomethane, chloroform, carbon tetrachloride, 1,2-dichloroethane, trichloroethylene and chlorobenzene; ethers, such as diethyl ether, methyl ethyl ether, diisopropyl ether, dibutyl ether, dioxane and tetrahyrofuran; nitriles, such as acetonitrile, propionitrile and benzonitrile; esters, such as ethyl acetate and amyl acetate; amides, such as dimethylformamide, N-methylpyrrolidone or hexamethylphosphoric acid triamide, as well as sulphones and sulphoxides, such as dimethyl sulphoxide and sulpholane.

The reaction variants (A) and (B) can be carried out over a wide temperature range. Generally, the temperature is between −20° C. and 100° C., as a rule at room temperature.

The reaction can be carried out at normal atmospheric pressure but it can also be carried out at higher or reduced pressures.

The compounds of the invention prepared by the above processes can be isolated from the reaction mixture in conventional manner, for example by distillation of the solvent at normal or reduced pressure, by precipitation with water or by extraction. A higher degree of purity can as a general rule be achieved by column chromatography or by recrystallisation.

The pyrazoline derivitives of the invention are colourless and odourless and in most cases, crystalline compounds. They are highly insoluble in water and toluene, slightly more soluble in ethyl acetate and highly soluble in dimethylformamide.

The preparation of the starting materials or formula II can be carried out in known manner according to the following reaction scheme.

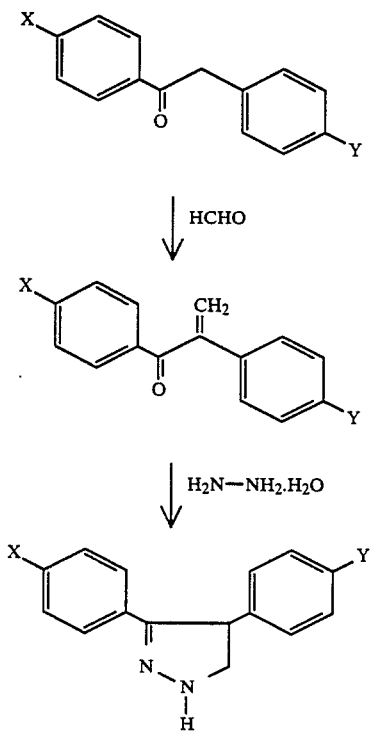

The ketones of general formula V are either known or can be prepared in known mannor.

In the case when X or Y is a haloalkoxy group, the preparation of ketone V can be carried out from the corresponding hydroxyketone Va or Vb

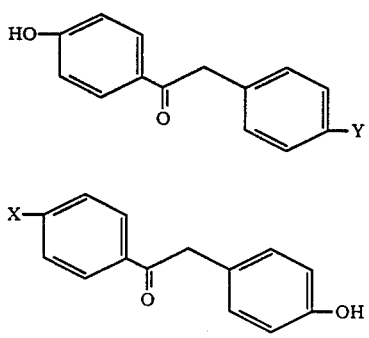

with an alkylating agent of formula R-A, according to usual methods, in which

A is a suitiable leaving group, such as for example chorine, bromine, iodine, p-toluenesulphonyloxy, methanesulphonyloxy or trifluromethylsulphonyloxy and R is a haloalkyl or haloalkylcycloalkyl group. The hydroxyketones Va or Vb are known or can be prepared according to known methods.

A further possibility for preparing the haloalkoxy substituted ketones of formula V is by the known conversion of the corresponding hydroxy compounds of formula Va or Vb with polyfluorinated olefines of general formula VI

in the presence of an acid binding substance. In this, B is halogen or a lower perfluoroalkyl group.

In the case when X or Y is a haloalkenyloxy group, the preparation of the ketone V can be carried out in known manner, either from the described haloalkoxy compounds by elimination of hydrogen halide in the presence of a strong base or by a substitution reaction or the hydroxy compound Va or Vb with a polyfluorinated olefine or formula VI.

In the case that X or Y is an optionally substituted phenoxy, phenylthio or haloalkylthio group, the ketone of formula V can be prepared in known manner by treatment of the benzene derivative VII

with a carboxylic acid or a carboxylic acid derivative of general formula VIII

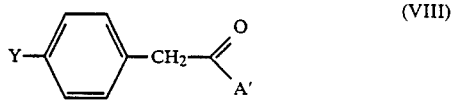

optionally in the presence of a Friedel-Crafts catalyst, in which A is suitable leaving group such as halogen, hydroxy or acyloxy.

The preparation of ketones of formula V in which X or Y is an optionally substituted pyridyloxy group can be carried out in known manner by treatment of the hydroxyketone Va or Vb with a halolpyridine in the presence of an acid binding substance.

Ketones of general formula V in which X or Y are sulphinyl or sulphonyl groups can be prepared by known methods from the corresponding thioethers by oxidation with a suitable oxidising agent such as for example hydrogen peroxide.

The compounds of the invention have insecticidal and acaricidal activity and are particularly useful in combating a variety of economically important insects, and acarids including animal ectoparasites. Examples include Lepidoptera, such as *Plutella xylostella, Spodoptera littoralis, Heliothis armigera* and *Pieris brassicae;* Diptera, such as *Musca domestica, Ceratitis capitata, Erioischia brassicae, Lucilia sericata* and *Aedes aegypti;* Homoptera, including aphids such as *Megoura viciae* and *Nilaparvata lugens;* Coleoptera, such as *Phaedon cochleariae, Anthonomus grandis* and *Epilachna varivestis* and corn rootworms (Diabrotica spp., e.g. *Diabrotica undecimpunctata*); Orthoptera, such as cockroaches e.g.

*Blattella germanica;* Hymenoptera, such as ants e.g. Monomorium pharaonis; mange mites, e.g. Sarcoptes spp.; ticks, such as *Boophilus microplus* and lice, such as *Damalinia bovis* and *Linognathus vituli;* as well as spider mites such as *Tetranychus urticae* and *Panonychus ulmi.*

The compounds of the invention are distinguished by a surprisingly high level of activity against important pest species, especially pest insects, which represents a valuable improvement in the art.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may include phospholipids, e.g. phosphatidylcholine, hydrated phosphatidylcholines, phosphatidylethanolamine, N-acyl-phosphatidylethanolamines, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example, water, aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

Formulations can be prepared, for example, from the following ingredients.

A WETTABLE POWDER
20 percent by weight active ingredient
35 percent by weight bentonite
8 percent by weight calcium lignosulphonate
2 percent by weight of the sodium salt of N-methyl-N-oleyltaurine
35 percent by weight silicic acid B PASTE
45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water C EMULSIFIABLE CONCENTRATE
20 percent by weight active ingredient
75 percent by weight isophorone
5 percent by weight of an emulsifier mixture of calcium phenylsulphonate and fatty alcohol polyglycol ether The following examples illustrate the preparation of compounds according to the invention.

EXAMPLE 1

3-[(4-Fluorophenoxy)phenyl]-N,4-bis-(4-fluorophenyl)-4,5-dihydropyrazole-1-carboxamide 3-[(4-Fluorophenoxy)phenyl]-4-(4-fluorophenyl)-4,5-dihydropyrazole (3 g; 8.6 mmol) was dissolved in dichloromethane (25 ml) and treated with 4-fluorophenyl isocyanate (1.04 g; 7.6 mmol), with stirring at room temperature. After an hour, the reaction mixture was filtered through silica gel, the filtrate was concentrated and treated with diisopropyl ether (50 ml). The precipitated crystals were separated and dried in vacuo (100 Torr).

Yield: 2.2 g (59% of theory)
Mp: 108° C.

EXAMPLE 2

N,4-Bis-(4-chlorophenyl)-3-{4-[(3-chloro-5-trifluoromethyl)-2-pyridyloxy]phenyl}4,5-dihydropyrazole-1-carboxamide This was prepared in a similar manner to that described in Example 1.
Mp: 153° C.

Preparation of the starting material 4-(4-Chlorophenyl)-3-{4-[(3-chloro-5-trifluoromethyl)-2-pyridyloxy]phenyl}4,5-dihydropyrazole 2,3-Dichloro-5-trifluoromethylpyridine (15.1 g; 0.07 mol), dissolved in dimethylformamide (20 ml) was added, dropwise, to a mixture of 4-chlorobenzyl-4'-hydroxyphenyl ketone (17.3 g; 0.07 mol) and potassium carbonate (11.6 g; 0.084 mol) in dimethylformamide (50 ml). The mixture was stirred for 3 hours at room temperature and then poured into ice-water (250 ml). The precipitated crystals were separated and recrystallised from ethanol to give pure 4-chlorobenzyl 4'-[(3-chloro-5-trifluoromethyl)-2-pyridyloxy]phenyl ketone.

Yield: 19.9 g (67% of theory)
Mp: 106° C.

A mixture of this product (8.5 g; 0.02 mol), aqueous formaldehyde (7.2 ml of a 37% solution), piperidine (0.3 ml) and acetic acid (0.3 ml) in methanol (50 ml) was heated at reflux for one hour. The reaction mixture was concentrated in a rotary evaporator, treated with water (100 ml) and extracted with dichloromethane (33 × 100 ml). The organic phase was dried over magnesium sulphate and concentrated in a rotary evaporator. The oily residue, without further purification, was taken up in ethanol (30 ml) and treated with hydrazine hydrate (3 ml) and the mixture heated at 60° C. for 5 minutes. After cooling, the precipitated crystals were separated and washed with cold ethanol. The crude material, so obtained, was used without further purification.

Yield: 5.8 g (64% of theory)
$^1$H-NMR: (CDCl$_3$, TMS, 80 MHz, ppm) 3.3–4.6 (3 H, m), 6.8–7.7 (8 H, m, Phenyl-H), 7.8–8.3 (2 H, m, Pyridyl-H).

EXAMPLE 3

4-Phenyl-3-[4-(2,2,2-trifluoroethylthio)phenyl]-N-(4-trifluoromethylphenyl)-4,5-dihydropyrazole-1-carboxamide This was prepared in a similar manner to that described in Example 1.

Mp: 154°–5° C.

Preparation of the starting material 4-Phenyl-3-[4-(2,2,2-trifluoroethylthio)phenyl]-N-(4-trifluoromethylphenyl)-4,5-dihydropyrazole 2,2,2-Trifluoroethylthiobenzene (28.8 g); 0.15 mol) was added, dropwise, over 20 minutes with stirring, to a mixture of aluminium trichloride (22 g; 0.165 mol) and phenylacetyl chloride (23.2 g; 0.15 mol) in dichloromethane (150 ml) kept cool with ice. The mixture was then stirred at room temperature for 30 minutes and added to ice water (1000 ml), extracted with dichloromethane (2×300 ml) and the purified organic phase was washed with water. After drying over magnesium sulphate the solvent was distilled. Recrystallisation from ethanol gave pure benzyl 4-(2,2,2-trifluoroethylthio)phenyl ketone.

Yield: 25.3 g (55% of theory)
Mp: 60°–1° C.

This was then treated with hydrazine hydrate in a similar manner to that described in Example 2 to give the title starting material.

$^1$H-NMR: (CDCl$_3$, TMS, 80 MHz, ppm) 3.4 (2 H, q, J=5 Hz), 3.3–4.6 (3 H, m) 7.2–7.7 (9 H, m).

EXAMPLE 4

N-(4-Chlorophenyl)-4-(4-(fluorophenyl)-3-[4-(2,2,3,3-tetrafluoropropoxy)phenyl]-4,5-dihydropyrazole-1-carboxamide This was prepared in a similar manner to that described in Example 1.
Mp: 163° C.

EXAMPLE 5

N-(4-Bromophenyl)-4-phenyl-3-[4-(2,2-difluorovinyloxy)phenyl]-4,5-dihydropyrazole-1-carboxamide This was prepared in a similar manner to that described in Example 1.
Mp: 153°–5° C.

Preparation of the starting material 3-[4-(2,2-difluorovinyloxy)phenyl]-4-phenyl-4,5-dihydropyrazole Butyllithium (190 ml; 1.6N) in hexane was added, dropwise, to diisopropylamine (30.4 g; 0.3 mol) in tetrahydrofuran (400 ml) kept under nitrogen at 0° C. The mixture was stirred for 30 minutes at 0° C. and then cooled to −70° C. At this temperature benzyl 4-(2,2,2-trifluoroethoxy)phenyl ketone, dissolved in tetrahydrofuran (70 ml) was slowly added, dropwise, to the reaction mixture. The solution became deep red. The mixture was then stirred at −70° C. for an hour and acetic acid (20 ml) was added, dropwise, without allowing the temperature of the reaction mixture to rise above −65° C. The mixture was then warmed to room temperature and added to ice-water (2000 ml). It was extracted with diethyl ether (3×500 ml) and the purified organic phase washed with sodium hydrogen carbonate, dried over magnesium sulphate and concentrated in a rotary evaporator. The residue was recrystallised from ethanol to give pure benzyl 4-(2,2-difluorovinyloxy)phenyl ketone.

Yield: 17.1 g (64% of theory)
Mp: 81°–5° C.

This was then treated with hydrazine hydrate in a similar manner to that described in Example 2 to give the title starting material.

$^1$H-NMR: (CDCl$_3$, TMS, 80 MHz, ppm) 3.3–4.6 (3 H, m), 6.0 (1 H, dd, J$_1$=15 Hz, J$_2$=3.5 Hz) 7.0–7.7 (9 H, m).

EXAMPLE 6

N-(4-Chlorophenyl)-4-(4-fluorophenyl)-3-[4-(1,1,2,3,3,3-hexafluoropropoxy)phenyl]-4,5-dihydropyrazole-1-carboxamide This was prepared in a similar manner to that described in Example 1.

$^1$H-NMR: (CDCl$_3$, TMS, 80 MHz, ppm) 3.9–4.9 (3 H, m), 6.0 (1 H, doublet 45 Hz, sextet 6 Hz), 6.9–7.8 (12 H, m), (1 H, s).

Preparation of starting material 4-(4-Fluorophenyl-3-[4-(1,1,2,3,3,3-hexafluoropropoxy)phenyl]-4,5-dihydroxypyrazole Sodium hydride (2.88 g of an 80% suspension in paraffin; 0.1 mol) was added to tetrahydrofuran (300 ml). 4-fluorobenzyl 4'-hydroxyphenyl ketone, dissolved in tetrahydrofuran (200 ml) was added dropwise to this, with stirring and under ice-cooling. After gas had stopped evolving, the mixture was cooled to −50° C. The apparatus was evacuated to ca. 100 Torr, with stirring, and hexafluoropropene (36 g; 0.24 mol) was bubbled through. The mixture was stirred for an hour at −50° C., allowed to warm to room temperature over 2 hours and then stirred at room temperature for 14 hours. The reaction mixture was added to ice-water (1000 ml) and extracted with dichloromethane (3×250 ml). The purified organic phase was washed with caustic soda (2×100 ml of 5% solution) and with water (200 ml), dried over magnesium sulphate and concentrated in a rotary evaporator. The residue was recrystallised from ethanol to give pure 4-fluorobenzyl 4'-(1,1,2,3,3,3-hexafluoropropoxy)phenyl ketone as colourless crystals
Yield: 56 g (72% of theory) MP: 38° C.

This was then treated with hydrazine hydrate in a similar manner to that described in Example 2 to give the title starting material.

$^1$H-NMR; (CDCl$_3$, TMS, 80 MHz, ppm) 3.3–4.6 (3 H, m), 5.0 (1 H, doublet 45 Hz, sextet 6 Hz), 6.9–7.8 (8 H, m).

In a similar manner the following compounds were obtained

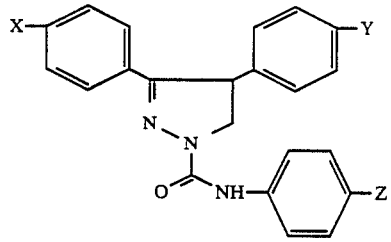

| Example No. | X | Y | Z | m.p. (°C.) |
| --- | --- | --- | --- | --- |
| 7 | 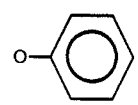 O— | H | F | 110–112 |
| 8 | 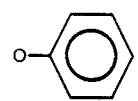 O— | H | Cl | 133–134 |

-continued
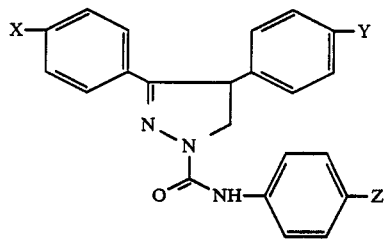
| Example No. | X | Y | Z | m.p. (°C.) |
|---|---|---|---|---|
| 9 | PhO- | H | CF$_3$ | 167–168 |
| 10 | PhO- | H | H | 147–149 |
| 11 | PhO- | H | Br | 143–144 |
| 12 | PhO- | H | CO$_2$Pr$^i$ | 163–165 |
| 13 | PhO- | H | OCHF$_2$ | 128–130 |
| 14 | PhO- | Cl | F | 121–123 |
| 15 | PhO- | Cl | Cl | 160–162 |
| 16 | PhO- | Cl | CF$_3$ | 163–164 |
| 17 | PhO- | Cl | H | 153 |
| 18 | PhO- | Cl | CO$_2$Pr$^i$ | 170–172 |
| 19 | PhO- | Cl | OCHF$_2$ | 147–150 |
-continued
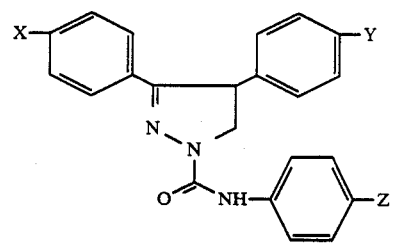
| Example No. | X | Y | Z | m.p. (°C.) |
|---|---|---|---|---|
| 20 | PhO- | F | F | 66 |
| 21 | PhO- | F | Cl | 112 |
| 22 | PhO- | F | CF$_3$ | 108 |
| 23 | PhO- | F | H | 143 |
| 24 | PhO- | F | Br | 161 |
| 25 | PhO- | F | CO$_2$Pr$^i$ | 194 |
| 26 | PhO- | F | OCHF$_2$ | 146 |
| 27 | PhO- | OCHF$_2$ | F | 139 |
| 28 | PhO- | OCHF$_2$ | Cl | 151 |
| 29 | PhO- | OCHF$_2$ | CF$_3$ | 148 |
| 30 | PhO- | OCHF$_2$ | H | 148 |

-continued
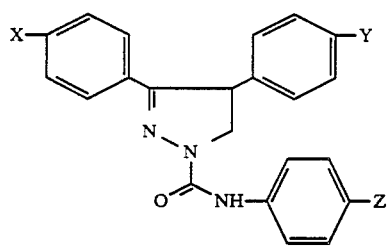
| Example No. | X | Y | Z | m.p. (°C.) |
|---|---|---|---|---|
| 31 | 4-PhO-C6H4 | OCHF2 | Br | 144 |
| 32 | 4-PhO-C6H4 | OCHF2 | CO2Pr$^i$ | 101 |
| 33 | 4-PhO-C6H4 | OCHF2 | OCHF2 | 133 |
| 34 | 4-(4-Cl-PhO)-C6H4 | H | F | 143 |
| 35 | 4-(4-Cl-PhO)-C6H4 | H | Cl | 146 |
| 36 | 4-(4-Cl-PhO)-C6H4 | H | CF3 | 155 |
| 37 | 4-(4-Cl-PhO)-C6H4 | H | H | 168 |
| 38 | 4-(4-Cl-PhO)-C6H4 | H | Br | 118 |
| 39 | 4-(4-Cl-PhO)-C6H4 | H | CO2Pr$^i$ | 105 |
| 40 | 4-(4-Cl-PhO)-C6H4 | Cl | F | 121 |
| 41 | 4-(4-Cl-PhO)-C6H4 | Cl | Cl | 156 |
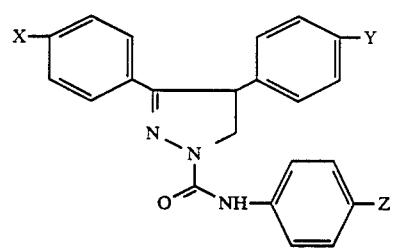
| Example No. | X | Y | Z | m.p. (°C.) |
|---|---|---|---|---|
| 42 | 4-(4-Cl-PhO)-C6H4 | Cl | CF3 | 154 |
| 43 | 4-(4-Cl-PhO)-C6H4 | Cl | H | 150 |
| 44 | 4-(4-Cl-PhO)-C6H4 | Cl | Br | 177 |
| 45 | 4-(4-Cl-PhO)-C6H4 | Cl | CO2Pr$^i$ | 103 |
| 46 | 4-(4-Cl-PhO)-C6H4 | F | F | 143 |
| 47 | 4-(4-Cl-PhO)-C6H4 | F | Cl | 118 |
| 48 | 4-(4-Cl-PhO)-C6H4 | F | CF3 | 141 |
| 49 | 4-(4-Cl-PhO)-C6H4 | F | H | 123 |
| 50 | 4-(4-Cl-PhO)-C6H4 | F | Br | 132 |
| 51 | 4-(4-Cl-PhO)-C6H4 | F | CO2Pr$^i$ | 164 |
| 52 | 4-(4-Cl-PhO)-C6H4 | F | OCHF2 | 114 |

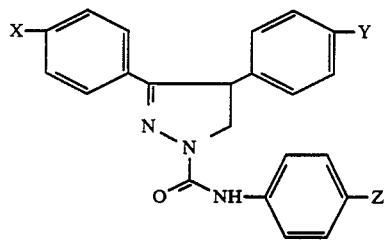
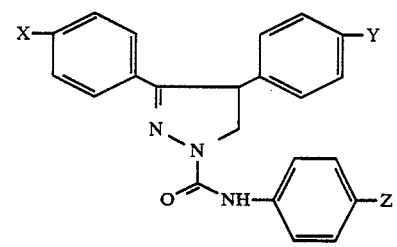
| Example No. | X | Y | Z | m.p. (°C.) | Example No. | X | Y | Z | m.p. (°C.) |
|---|---|---|---|---|---|---|---|---|---|
| 53 | 4-Cl-C₆H₄-O- | OCHF₂ | F | 143–144 | 64 | 4-F-C₆H₄-O- | H | CO₂Pr$^i$ | 117 |
| 54 | 4-Cl-C₆H₄-O- | OCHF₂ | Cl | 127–129 | 65 | 4-F-C₆H₄-O- | H | OCHF₂ | 151 |
| 55 | 4-Cl-C₆H₄-O- | OCHF₂ | CF₃ | 115–117 | 66 | 4-F-C₆H₄-O- | Cl | F | 134 |
| 56 | 4-Cl-C₆H₄-O- | OCHF₂ | H | 145–147 | 67 | 4-F-C₆H₄-O- | Cl | Cl | 174 |
| 57 | 4-Cl-C₆H₄-O- | OCHF₂ | Br | 128–130 | 68 | 4-F-C₆H₄-O- | Cl | CF₃ | 152 |
| 58 | 4-Cl-C₆H₄-O- | OCHF₂ | OCHF₂ | 118–120 | 69 | 4-F-C₆H₄-O- | Cl | H | 149 |
| 59 | 4-F-C₆H₄-O- | H | F | 120 | 70 | 4-F-C₆H₄-O- | Cl | Br | 186 |
| 60 | 4-F-C₆H₄-O- | H | Cl | 133 | 71 | 4-F-C₆H₄-O- | Cl | CO₂Pr$^i$ | 132 |
| 61 | 4-F-C₆H₄-O- | H | CF₃ | 172 | 72 | 4-F-C₆H₄-O- | Cl | OCHF₂ | 145 |
| 62 | 4-F-C₆H₄-O- | H | H | 157 | 73 | 4-F-C₆H₄-O- | F | Cl | 135 |
| 63 | 4-F-C₆H₄-O- | H | Br | 146 | 74 | 4-F-C₆H₄-O- | F | CF₃ | 135 |

-continued
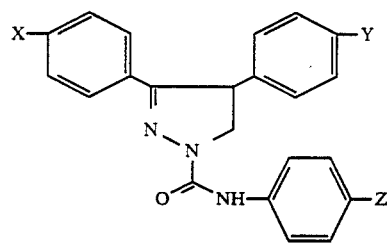
| Example No. | X | Y | Z | m.p. (°C.) |
|---|---|---|---|---|
| 75 |  | F | H | 144 |
| 76 |  | F | Br | 148 |
| 77 |  | F | CO$_2$Pr$^i$ | 161 |
| 78 |  | F | OCHF$_2$ | 132 |
| 79 |  | OCHF$_2$ | F | 147 |
| 80 |  | OCHF$_2$ | Cl | 128 |
| 81 |  | OCHF$_2$ | CF$_3$ | 131 |
| 82 |  | OCHF$_2$ | H | 158 |
| 83 |  | OCHF$_2$ | Br | 127 |
| 84 |  | OCHF$_2$ | OCHF$_2$ | 124 |
| 85 |  | H | F | 162 |
-continued
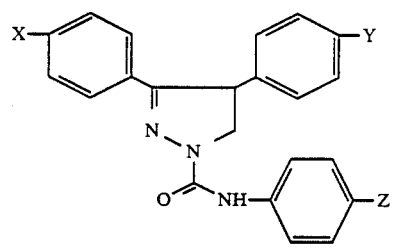
| Example No. | X | Y | Z | m.p. (°C.) |
|---|---|---|---|---|
| 86 |  | H | Cl | 165 |
| 87 |  | H | CF$_3$ | 170 |
| 88 |  | H | OCHF$_2$ | 156 |
| 89 |  | Cl | F | 151 |
| 90 |  | Cl | Cl | 179 |
| 91 |  | Cl | OCHF$_2$ | 148 |
| 92 |  | F | F | 154 |
| 93 |  | F | Cl | 129 |
| 94 |  | F | CF$_3$ | 159 |
| 95 |  | F | Br | 133 |
| 96 |  | F | OCHF$_2$ | 144 |
| 97 | OCH$_2$CF$_2$CHF$_2$ | H | Cl | 152-153 |

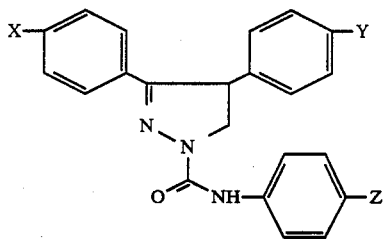
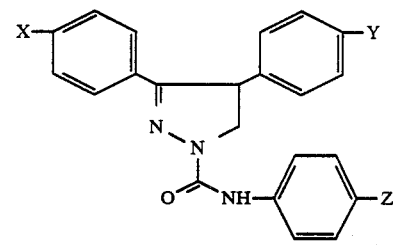

| Example No. | X | Y | Z | m.p. (°C.) |
|---|---|---|---|---|
| 98 | OCH₂CF₂CHF₂ | H | CF₃ | 143–144 |
| 99 | OCH₂CF₂CHF₂ | H | F | 148–149 |
| 100 | OCH₂CF₂CHF₂ | H | Br | 95–98 |
| 101 | OCH₂CF₂CHF₂ | H | OCHF₂ | 135–137 |
| 102 | OCH₂CF₂CHF₂ | Cl | Cl | 123–125 |
| 103 | OCH₂CF₂CHF₂ | Cl | CF₃ | 119–120 |
| 104 | OCH₂CF₂CHF₂ | Cl | F | 160–162 |
| 105 | OCH₂CF₂CHF₂ | Cl | OCHF₂ | 175–177 |
| 106 | OCH₂CF₂CHF₂ | F | CF₃ | 158 |
| 107 | OCH₂CF₂CHF₂ | F | F | 140 |
| 108 | OCH₂CF₂CHF₂ | F | Br | 165 |
| 109 | OCH₂CF₂CHF₂ | F | OCHF₂ | 163 |
| 110 | OCH=CF₂ | H | Cl | 152–155 |
| 111 | OCH=CF₂ | H | CF₃ | 192–195 |
| 112 | OCH=CF₂ | H | F | 139–141 |
| 113 | OCH=CF₂ | H | OCHF₂ | 125–126 |
| 114 | OCH=CF₂ | H | H | 118–119 |
| 115 | OCH=CF₂ | Cl | Cl | 159–160 |
| 116 | OCH=CF₂ | Cl | F | 177–178 |
| 117 | OCH=CF₂ | Cl | Br | 155–157 |
| 118 | OCH=CF₂ | Cl | OCHF₂ | 140 |
| 119 | OCH=CF₂ | F | Cl | 137–139 |
| 120 | OCH=CF₂ | F | CF₃ | 150 |
| 121 | OCH=CF₂ | F | F | 138 |
| 122 | OCH=CF₂ | F | OCHF₂ | 107 |
| 123 | OCF₂CHFCF₃ | F | F | oil |
| 124 | 3-Cl-5-CF₃-2-pyridyloxy | Cl | CF₃ | 173 |
| 125 | 3-Cl-5-CF₃-2-pyridyloxy | Cl | F | 127 |
| 126 | 3-Cl-5-CF₃-2-pyridyloxy | H | F | 172 |
| 127 | 3-Cl-5-CF₃-2-pyridyloxy | H | Cl | 137 |
| 128 | 3-Cl-5-CF₃-2-pyridyloxy | H | CF₃ | 172 |
| 129 | C₆H₅S | F | Cl | 153 |
| 130 | C₆H₅S | F | CF₃ | 179 |
| 131 | C₆H₅S | F | F | 136 |
| 132 | C₆H₅S | F | Br | 157 |
| 133 | C₆H₅S | F | H | 169 |
| 134 | C₆H₅S | F | OCHF₂ | 144 |
| 135 | C₆H₅S | OCHF₂ | F | 167–168 |
| 136 | C₆H₅S | OCHF₂ | Cl | 134–135 |
| 137 | C₆H₅S | OCHF₂ | CF₃ | 129–130 |
| 138 | C₆H₅S | Cl | Cl | 153–155 |
| 139 | C₆H₅S | Cl | CF₃ | 169–170 |

-continued

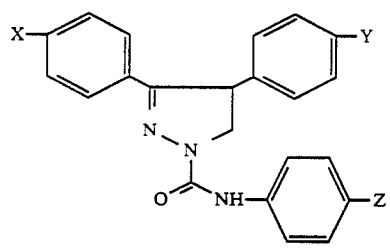
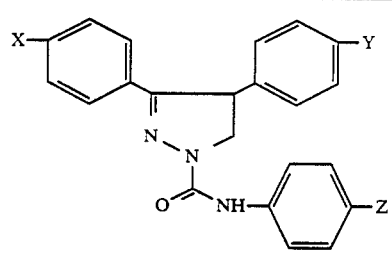

| Example No. | X | Y | Z | m.p. (°C.) |
|---|---|---|---|---|
| 140 | PhS- | Cl | F | 133–134 |
| 141 | PhS- | Cl | H | 145–146 |
| 142 | PhS- | Cl | Br | 159–160 |
| 143 | PhS- | Cl | OCHF$_2$ | 140–141 |
| 144 | PhS- | H | Cl | 163–164 |
| 145 | PhS- | H | CF$_3$ | 170–171 |
| 146 | PhS- | H | F | 123–124 |
| 147 | PhS- | H | H | 156–157 |
| 148 | PhS- | H | Br | 158–159 |
| 149 | PhS- | H | OCHF$_2$ | 119–120 |
| 150 | SCH$_2$CF$_3$ | H | Cl | 178–179 |
| 151 | SCH$_2$CF$_3$ | H | F | 165–166 |
| 152 | SCH$_2$CF$_3$ | H | H | 140–141 |
| 153 | SCH$_2$CF$_3$ | H | Br | 176–177 |
| 154 | SCH$_2$CF$_3$ | H | OCHF$_2$ | 119–120 |
| 155 | SCH$_2$CF$_3$ | F | Cl | 118–119 |
| 156 | SCH$_2$CF$_3$ | F | CF$_3$ | 122–123 |
| 157 | SCH$_2$CF$_3$ | F | F | 123–124 |
| 158 | SCH$_2$CF$_3$ | F | H | 115–116 |
| 159 | SCH$_2$CF$_3$ | F | Br | 115–116 |
| 160 | SCH$_2$CF$_3$ | F | OCHF$_2$ | 111–112 |
| 161 | 4-Br-C$_6$H$_4$-O- | F | Cl | 83–85 |
| 162 | 4-Br-C$_6$H$_4$-O- | F | CF$_3$ | 126–128 |
| 163 | 4-Br-C$_6$H$_4$-O- | F | F | 129–130 |
| 164 | 4-Br-C$_6$H$_4$-O- | F | H | 140–141 |
| 165 | 4-Br-C$_6$H$_4$-O- | F | Br | 125–126 |
| 166 | 4-Br-C$_6$H$_4$-O- | F | OCHF$_2$ | 106–107 |
| 167 | OCF$_2$CHFCF$_3$ | F | OCHF$_2$ | scum |
| 168 | OCF$_2$CHFCF$_3$ | F | CF$_3$ | scum |
| 169 | OCF$_2$CHFCF$_3$ | F | H | scum |
| 170 | OCF$_2$CHFCF$_3$ | F | Br | scum |
| 171 | PhS- | OCHF$_2$ | Br | 147–148 |
| 172 | PhS- | OCHF$_2$ | OCHF$_2$ | 138–139 |
| 173 | 3-Cl-5-CF$_3$-2-pyridyl-O- | F | F | 100 |

-continued

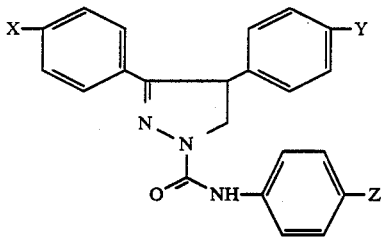

| Example No. | X | Y | Z | m.p. (°C.) |
|---|---|---|---|---|
| 174 | ![Cl-pyridyl-O-CF3] | F | Cl | 113 |
| 175 | ![Cl-pyridyl-O-CF3] | F | CF₃ | 186 |

EXAMPLE 176

N-(4-Chlorophenyl)-3-[4-(2,2-difluorocyclopropylmethoxy)phenyl]-4-(4-fluorophenyl-4,5-dihydropyrazole-1-carboxamide This was prepared in a similar manner to that described in Example 1.
Mp: 150°-1° C.

Preparation of the starting material 3-[4-(2,2-difluorocyclopropylmethoxy)phenyl]-4-(4-fluorophenyl-4,5-dihydropyrazole 2,2-Difluorocyclopropylmethyl bromide (17.1 g; 0.1 mol) was added, dropwise, to a mixture of 4 fluorobenzyl 4′-hydroxyphenyl ketone (23 g; 0.1 mol) and potassium carbonate (15.2 g; 0.11 mol) and sodium iodide (2 g) in dimethylformamide (70 ml) at 80° C. The mixture was stirred for 3 hours at this temperature and after cooling, poured into ice-water (300 ml). The residue was separated and recrystallised from diisopropyl ether to give pure 4-(2,2-difluorocyclopropylmethoxy)phenyl 4′-fluorobenzyl ketone as colourless crystals.

Yield: 23.3 g (72.7% of theory)
Mp: 93° C.

This was then treated with hydrazine hydrate in a similar manner to that described in Example 2 to give the title starting material.

$^1$H-NMR: (CDCl₃, TMS, 80 MHz, ppm) 1.0–2.3 (3 H, m, cyclopropyl H), 3.3–4.6 (5 H, m), 7.2–7.7 (8 H, m).

EXAMPLE 178

3,4-Bis-(4-Chlorophenyl)-N-[4-(2,2-difluorocyclopropyloxy)phenyl]-4,5-dihydropyrazole-1carboxamide 4-(2,2-Difluorocyclopropyloxy)aniline was dissolved in dioxane (10 ml) and treated with tricloromethyl chloroformate (0.6 ml). The mixture was heated at 100° C. for 3 hours whilst excluding moisture. The mixture was then cooled to room temperature and 3,4-bis-(4-chlorophenyl)-4,5-dihydropyrazole (2.64 g; 9 mmol), dissolved in dichloromethane (30 ml), was added with stirring. After 3 hours the reaction mixture was concentrated and the residue chromatographed on silica gel.

Yield: 2.67 g (59% of theory)
Mp: 187°-8° C.

EXAMPLE 178

N-(4-Chlorophenyl)-4-phenyl-3-[4-(2,2,2-trifluoroethoxy)phenyl]-4,5-dihydropyrazole-1-carboxamide This was prepared in a similar manner to that described in Example 1.
Mp: 183° C.

Preparation of the starting material 4-phenyl-3-[4-(2,2,2-trifluoroethoxy)phenyl]-4,5-dihydropyrazole A mixture of benzyl 4-hydroxyphenyl ketone (12.5 g; 0.059 mol), potassium carbonate (11.2 g; 0.08 mol) and sodium iodide (0.5 g) in dimethylformamide (80 ml) was heated to 130° C. At this temperature, 2,2,2-trifluoroethyl p-toluenesulphonate (16.4 g; 0.066 mol), dissolved in dimethyl sulphoxide (30 ml), was added dropwise over 30 minutes. It was then stirred for 45 minutes at a 130° C. After cooling, the reaction mixture was poured into ice-water (500 ml) and the precipitate separated. This was recrystallised from diisopropyl ether/hexane to give pure benzyl 4-(2,2,2-trifluoroethoxy)phenyl ketone.

Yield: 13.5 g (77.7% of theory)
Mp: 108° C.

This was then treated with hydrazine hydrate in a similar manner to that described in Example 2 to give the title starting material.

$^1$H-NMR: (CDCl₃, TMS, 80 MHz, ppm) 3.3–4.6 (3 H, m), 4.25 (2 H, q, J=8 Hz, —OCH₂—CF₃), 4.0–6.6 (1 H, very wide signal, N-H), 6.7 (2 H, d, J=9 Hz), 7.2 (5 H, s), 7.45 (2 H, d, J=9 Hz)

In a similar manner the following compounds were obtained

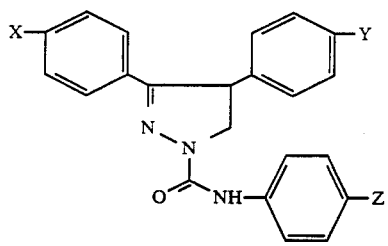
| Example No. | X | Y | Z | m.p. (°C.) |
|---|---|---|---|---|
| 179 | F | F |  | 128 |
| 180 | 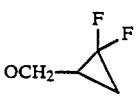 (OCH₂-cyclopropyl-F,F) | Cl | C(CH₃)₃ | 190-94 |
| 181 | " | " | Cl | 168-69 |
| 182 | " | " | CF₃ | 95-98 |
| 183 | " | " | H | 144-47 |
| 184 | " | " | F | 120 |
| 185 | " | " | Br | 98-102 |
| 186 | " | " | CO₂Pr$^i$ | 147-49 |
| 187 | " | F | H | 134-36 |
| 188 | " | " | CF₃ | 153 |
| 189 | " | " | F | 68 |
| 190 | 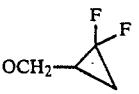 | " | Br | 145-46 |
| 191 | " | " | CO₂Pr$^i$ | 128 |
| 192 | " | " | OCHF₂ | 154-55 |
| 193 | " | H | Cl | 134 |
| 194 | " | " | CF₃ | 135-37 |
| 195 | Cl | 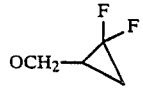 | C(CH₃)₃ | 140-42 |
| 196 | " | " | CF₃ | 141-44 |
| 197 | H | " | Cl | 125-27 |
| 198 | " | " | CF₃ | 133 |
| 199 | " | " | H | 145-46 |
| 200 | " | " | F | 118 |
| 201 | " | 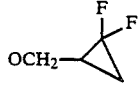 | Br | 148-50 |
| 202 | " | " | CO₂Pr$^i$ | 100 |
| 203 | Cl | Cl | 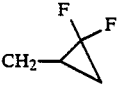 | 150-51 |
| 204 | " | H | " | 157-59 |
| 205 | " | " | 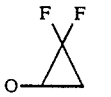 | 188-90 |
| 206 | 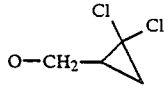 (O-CH₂-cyclopropyl-Cl,Cl) | F | Cl | 104 |

-continued

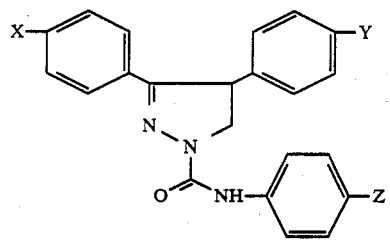

| Example No. | X | Y | Z | m.p. (°C.) |
|---|---|---|---|---|
| 207 | " | " | CF$_3$ | 143 |
| 208 | " | " | F | 94 |
| 209 | " | " | Br | 141 |
| 210 | Cl$_2$-cyclopropyl-CH$_2$-O— | F | OCHF$_2$ | 150–52 |
| 211 | " | " | H | 70 |
| 212 | " | " | CO$_2$Pr$^i$ | 70 |
| 213 | OCH$_2$CF$_3$ | H | CF$_3$ | 164–66 |
| 214 | " | " | F | 177 |
| 215 | " | " | CO$_2$Pr$^i$ | 193 |
| 216 | " | Cl | Cl | 143 |
| 217 | " | " | CF$_3$ | 152 |
| 218 | OCH$_2$CF$_3$ | Cl | F | 182–84 |
| 219 | " | " | CO$_2$Pr$^i$ | 188–191 |
| 220 | " | " | Br | 145–46 |
| 221 | " | " | OCHF$_2$ | 183 |
| 222 | OCH$_2$CF$_3$ | F | Cl | 180 |
| 223 | " | " | CF$_3$ | 155 |
| 224 | " | " | CO$_2$Pr$^i$ | 159–60 |
| 225 | " | " | H | 140–41 |
| 226 | " | " | Br | 170–72 |
| 227 | " | " | F | 156–57 |
| 228 | " | " | OCF$_2$CHF$_2$ | 175 |
| 229 | " | " | OCHF$_2$ | 153–54 |
| 230 | F$_2$-cyclopropyl-CH$_2$-O— | Cl | OCHF$_2$ | 168 |
| 231 | " | " | OCF$_2$CHF$_2$ | 167 |
| 232 | " | H | H | 156–158 |
| 233 | " | " | F | 163–165 |
| 234 | " | " | Br | 154–155 |
| 235 | " | " | OCHF$_2$ | 161 |
| 236 | " | " | OCF$_2$CHF$_2$ | 180 |
| 237 | F | F$_2$-cyclopropyl-CH$_2$-O— | Cl | 121–123 |
| 238 | " | " | CF$_3$ | 140–142 |
| 239 | " | " | F | 123 |
| 240 | " | " | OCHF$_2$ | 110 |
| 241 | H | " | OCHF$_2$ | 120 |
| 242 | OCH$_2$CF$_3$ | H | Br | 185 |
| 243 | " | " | OCHF$_2$ | 145 |
| 244 | Cl | F$_2$-cyclopropyl-CH$_2$-O— | OCHF$_2$ | 144–145 |
| 245 | F$_2$-cyclopropyl-CH$_2$-O— | F | OCH$_2$CF$_3$ | 152 |

-continued

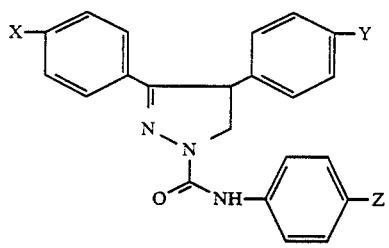

| Example No. | X | Y | Z | m.p. (°C.) |
| --- | --- | --- | --- | --- |
| 246 | F | Cl | O—⟨△⟩(F,F) | 159 |
| 247 | F | Cl | OCH₂—⟨△⟩(F,F) | 150 |
| 248 | F | F | O—⟨△⟩(F,F) | 140 |

The following Examples demonstrate the biological activity of the compounds of the invention.

TEST EXAMPLE A

Activity in prophylactic treatment of leaves against brown rice-hoppers (*Niliparvata lugens Stal*)

In a heated greenhouse, rice seedlings (about 15 per pot) were grown until formation of the third leaf and then sprayed until dripping wet with an aqueous preparation containing 0.1% of active material. After drying the sprayed leaves, a transparent cylinder was placed over each pot. 30 Adult brown rice-hoppers (*Niliparvata lugens*) were introduced into each pot. After 2 days at 26° C. in the greenhouse, the amount of dead hoppers was determined. The activity was calculated according to Abbott in comparison with several untreated control pots.

Activities of 80% and above were shown, for example, with the compounds of Example 2, 6, 54, 95, 97, 101, 113, 115, 116, 119–122, 129–140, 143, 146–150, 152, 156 and 160.

TEST EXAMPLE B

Activity in curative treatment of broad beans (Vicia fabae L.) against black bean aphids (Aphis fabae scop.)

In a heated greenhouse, broad bean (Vicia fabae L.) seedlings (one plate per pot) were grown until about 6 cm high. The plants were then treated with cultures of black bean aphids (Aphis fabae scop.). After the plants had been colonised with 100 to 200 adults, they were sprayed until dripping wet with aqueous preparations of each active material containing 0.1% of active material and put in a greenhouse at about 24° C. After 2 days, the amount of dead aphids was determined. The activity was calculated according to Abbott in comparison with several untreated control pots.

With the compounds of the invention of Examples 3, 57, 58, 85, 87, 88, 90, 91 115, 116, 118, 120, 122, 124, 128, 131–135, 138–143, 146–150, 152 and 153, an activity of at least 75% was achieved.

TEST EXAMPLE C

Activity in curative treatment of dwarf beans (Phaseolus vulgaris nanus Aschers.) against motile stages of the two spotted spider mite (Tetranychus urticae Koch).

In a heated greenhouse, dwarf bean seedlings were grown until full development of the primary leaf and then covered with pieces of leaf infested with *Tetranychus urticae*. One day later, the pieces of leaf were removed and the plants sprayed until dripping wet with aqueous preparations of each active material containing 0.1% of active material. After 7 days, at 22° C. to 24° C. the amount of dead motile stages of Tetranychus on the treated and on untreated plants were determined. From this the degree of activity after Abbott was calculated.

With the compounds of the invention of Examples 122 and 133 an activity of over 75% was achieved.

TEST EXAMPLE D

Activity in curative treatment of dwarf beans (Phaseolus vulgaris nanus Aschers.) against eggs of the two spotted spider mite (Tetranychus urticae Koch).

In a heated greenhouse, dwarf bean seedlings were grown until full development of the primary leaf and then treated with adult female *Tetranychus urticae*. One day later, following the laying of eggs, the plants were sprayed until dripping wet with aqueous preparations of each active material containing 0.1% of active material. After 7 days, at 22° C. to 24° C. the amount of dead eggs on treated and on untreated plants were determined. From this the degree of activity after Abbott was calculated.

With the compounds of the invention of Examples 2, 58, 116, 119, 122, 123, 133, 135, 147 and 152 an activity of over 75% was achieved.

TEST EXAMPLE E

Activity against larvae of diamond-backed moth (*Plutella xylostella*).

Compounds of the invention were made up at a concentration of 0.04%, by diluting with water to the desired concentration, either on acetone solution or an emulsifiable concentrate. Cabbage leaves (Brassica oleracea var. botrytis), placed in polystyrene petri dishes, were sprayed with these preparations (4 mg spray/cm²). After the sprayed surface had dried, 10 young larvae of the diamond-backed moth (Plutella xylostella) were placed in each petri dish and thereby exposed to the treated food in the closed dishes for two days. Feeding with untreated cabbage leaves then followed for a further three days. The % mortality of the larvae after five days indicated the level of activity.

In this experiment, the compounds of the invention according to Examples 1, 4, 8, 10, 11, 13, 14, 21, 23, 24, 26, 34–36, 39–43, 53, 54, 58–60, 63, 65, 67, 68, 70, 72–83, 88, 97–113, 115, 118–120, 129, 145, 146, 148, 176, 177, 181, 182, 185, 188–194, 196, 197, 198, 201, 205–210, 216–221, 223, 224, 227, 229 and 230 showed an activity of 90–100%.

TEST EXAMPLE F

Activity against larvae (L3) of the Mexican bean beetle (Epilachna varivestis)

Compounds of the invention were made up at a concentration of 0.04%, by diluting with water to the desired concentration, either an acetone solution or an emulsifiable concentrate. French bean plants (Phaseolus vulgaris) in the primary leaf stage were dipped in the preparations. For each test, three plant stems with 6 primary leaves were placed in glass vases filled with water and enclosed in plexiglass cylinders. Then 5 larvae of the Mexican bean beetle (Epilachna varivestis) at the third larval stage were put in the glass cylinders and kept for 5 days under extended daylight conditions. The % mortality of the larvae after 5 days indicated the level of activity.

In these experiments the compounds of Examples 1–6, 8 12, 14–16, 19–31, 33–36, 38, 39, 44, 46–48, 50–52, 55, 59–66, 72–74, 76–80, 82–84, 89–125, 129, 132, 140, 150, 153–160, 176, 178, 181, 182, 183, 187–191, 197, 198, 206–212, 216, 217, 220–224 and 226–229 caused 90 to 100% mortality.

TEST EXAMPLE G

Activity against larvae (L2) of the cotton army worm (Spodoptera littoralis)

Compounds of the invention were made up at a concentration of 0.04%, by diluting with water to the desired concentration, either an acetone solution or an emulsifiable concentrate. Leaflet pairs of beans (Vicia fabae) as wall as 10 larvae (L2) of the cotton army worm (Spodoptera littoralis) per experiment were sprayed with 4 mg spray/cm² of these preparations in polystyrene petri dishes. The closed petri dishes were left in the laboratory under extended daylight conditions for two days. Feeding with untreated bean leaves then followed for a further three days. The % mortality of the larvae after 5 days indicated the level of activity.

In these experiments the compounds of Examples 1, 4, 7, 8, 10, 11, 14, 15, 17, 19–25, 34, 35, 37, 40, 43, 46, 47, 49, 52, 53, 56, 59, 60, 62, 63, 65–67, 69, 70, 72–76, 78–80, 82, 83, 92, 96–116, 118–122, 140, 153–157, 160, 176, 177, 178, 181–185, 187–190, 192, 193, 194, 196, 197, 198, 207–211, 213, 214, 216, 217, 218, 220–223 and 226–229 caused 90 to 100% mortality.

TEST EXAMPLE H

Insecticidal and acaricidal activity against Boophilus microplus (1), Lucilia sericata (2) Musca domestica (3) and Blattella germanica (4).

1. 9 cm diameter filter papers were impregnated with 1 ml aliquots of acetone solutions of test compound at various concentrations. The papers were allowed to dry and then folded into envelopes in which cattle tick larvae, (Boophilus microplus) were enclosed and held at 25° C. and 80% R.H. for 48 hours. The percentage mortality of tick larvae was then recorded and compared with controls.

The controls gave a mortality of less than 5% whereas compounds of Examples 21, 23, 162 and 194 caused at least 50% mortality at a concentration of 1000 ppm or less.

2. 1 ml aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blowfly (Lucilia sericata), closed by a cotton wool plug and held at 25° C. for 24 hours. For the controls the mortality was <5% whereas the compounds of Examples 1, 2, 3, 5, 6, 9, 11–14, 19–29, 31, 33–37, 39, 40, 46–52, 56–61, 63–70, 72–74, 76–81, 91–96, 102–105, 112–116, 118, 121, 122, 124–127, 150, 115–170, 173–6, 178, 181–185, 188, 192–194, 206, 208, 209, 212–217, 219–224, 226–229, 233–241 and 244 had an $LC_{50}$ of 300 ppm or less.

3. Aliquots of acetone solutions of test compounds at various concentrations were applied to 9 cm diameter filter papers placed in the bottom of 9 cm diameter petri dishes closed by glass lids. After evaporation of solvent, the treated surfaced, together with control treated with acetone alone, were then infested with adult houseflies, (Musca domestica) and held at 22° C. for 24 hours.

The percentage mortality of the insects was then recorded. Less than 5% mortality resulted in the control treatments whereas the compounds of Examples 11, 13, 102, 103, 114–116, 213, 216, 217 and 220, 5, 9, 10 and 22–28 had an $LD_{50}$ of 1000 mg/m² or less.

4. Aliquots of acetone solutions of test compounds at various concentrations were applied to glass plates (10 cm×10 cm). After evaporation of solvent, the treated surfaces, together with controls treated with acetone alone, were then infested with second instar nymphs of the German cockroach, (Blattella germanica), retained on the treated surface within PTFE-coated glass rings 6 cm in diameter and held for 24 hours at 22° C. The percentage mortality of the insects was then recorded.

Less than 5% mortality resulted in the control treatments whereas the compounds of Examples 116 and 130 had an $LD_{50}$ of 1000 mg/m² or less.

We claim:

1. Pyrazoline derivative of the formula

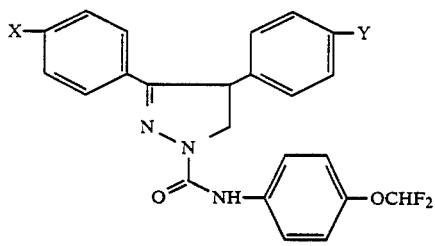

in which X is 2,2,2-trifluoroethoxy and Y is hydrogen or fluorine.

2. A compound according to claim 1 in which Y is hydrogen.

3. A compound according to claim 1 in which Y is fluorine.

4. An insecticidal or acaricidal composition which comprises an insecticidal or acaricidal effective amount of a compound claimed in claim 1, in admixture with an agriculturally acceptable diluent or carrier.

5. The composition of claim 4 in which Y is fluorine.

6. The composition according to claim 4 in which Y is hydrogen.

7. A method for combating insects or acarids which comprises applying to the insect, acarid or their locus an insecticidal or acaricidal effective amount of a compound claimed in claim 2.

8. The method of claim 7 in which Y is fluorine.

9. The method according to claim 7 in which Y is hydrogen.

* * * * *